(12) United States Patent
Castillo et al.

(10) Patent No.: US 6,444,710 B1
(45) Date of Patent: *Sep. 3, 2002

(54) USE OF CERTAIN FATTY ACID/AMINO ACID SOAPS TO ENHANCE ANTIMICROBIAL EFFECTIVENESS OF TOPICALLY ADMINISTRABLE PHARMACEUTICAL COMPOSITIONS

(75) Inventors: Ernesto J. Castillo, Arlington, TX (US); Steven Gerson, San Jose, CA (US); Wesley Wehsin Han, Arlington, TX (US)

(73) Assignee: Alcon Manufacturing, Ltd., Fort Worth, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 09/949,198

(22) Filed: Sep. 7, 2001

Related U.S. Application Data

(63) Continuation-in-part of application No. 09/399,013, filed on Sep. 21, 1999, now abandoned.
(60) Provisional application No. 60/105,855, filed on Oct. 27, 1998.

(51) Int. Cl.[7] .................. A01N 25/00; A61K 31/74; A61K 6/00
(52) U.S. Cl. .................. 514/975; 424/78.02; 424/401
(58) Field of Search .................. 514/975; 424/78.02, 424/401

(56) References Cited

U.S. PATENT DOCUMENTS

| | | | |
|---|---|---|---|
| 3,275,503 A | 9/1966 | Marnett et al. | 167/22 |
| 4,380,637 A | 4/1983 | Lindemann et al. | 548/112 |
| 4,485,029 A | 11/1984 | Kato et al. | 252/106 |
| 4,911,920 A | 3/1990 | Jani et al. | 424/78 |
| 5,000,868 A | 3/1991 | Wittpenn, Jr. et al. | 252/106 |
| 5,093,126 A | 3/1992 | Jani et al. | 424/428 |
| 5,397,567 A | 3/1995 | Lobering et al. | 424/78.04 |
| 5,494,937 A | 2/1996 | Asgharian et al. | 514/772.3 |
| 5,504,113 A | 4/1996 | Lucero | 514/554 |
| 5,520,920 A | 5/1996 | Castillo et al. | 424/402 |
| 5,536,305 A | 7/1996 | Yu | 106/18.33 |
| 5,540,918 A | 7/1996 | Castillo et al. | 424/78.04 |
| 5,631,218 A | 5/1997 | Allan et al. | 510/423 |
| 5,641,480 A | 6/1997 | Vermeer | 424/70.24 |
| 5,712,232 A * | 1/1998 | Moriyama et al. | 510/120 |
| 5,741,817 A | 4/1998 | Chowhan et al. | 514/561 |
| 6,146,622 A | 11/2000 | Castillo et al. | 424/78.02 |
| 6,211,238 B1 | 4/2001 | Castillo et al. | 514/563 |
| 6,284,749 B1 | 9/2001 | Castillo et al. | 514/159 |

FOREIGN PATENT DOCUMENTS

| | | |
|---|---|---|
| EP | 0 194 097 A1 | 9/1986 |
| EP | 0 243 145 A2 | 10/1987 |
| EP | 0 429 732 A1 | 6/1991 |
| JP | 9077725 | 3/1997 |
| WO | WO 00/24375 | 5/2000 |
| WO | WO 01/21209 | 3/2001 |

OTHER PUBLICATIONS

Cozzoli, *Preservative–Free and Self–Preserving cosmetics and Drugs: Principles and Practice*, Marcel Dekker, Inc., New York, NY, (1997), Chapter 4 "The Role of Surfactants in Self–Preserving Cosmetic Formulas".

Hamposyl Surfactants Product Brochure from Grace Organic Chemicals, Lexington, MA, Sep. 1992.

Vives et al., "Irritancy Potential Induced by Surfactants Derived from Lysine," *Toxicology in Vitro*, vol. 11; pp. 779–783 (1997).

* cited by examiner

Primary Examiner—Michael G. Hartley
Assistant Examiner—Michael A. Willis
(74) Attorney, Agent, or Firm—Patrick M. Ryan

(57) ABSTRACT

Fatty acid/amino acid soaps are used to enhance antimicrobial effectiveness in topically administrable pharmaceutical compositions containing at least one active ingredient, a cationic preservative and an anionic polyelectrolyte, such as a carboxyvinyl polymer, xanthan gum, polystyrene sulfonic acid polymer or cationic exchange resin.

17 Claims, No Drawings

USE OF CERTAIN FATTY ACID/AMINO ACID SOAPS TO ENHANCE ANTIMICROBIAL EFFECTIVENESS OF TOPICALLY ADMINISTRABLE PHARMACEUTICAL COMPOSITIONS

This application is a continuation-in-part application of U.S. Ser. No. 09/399,013, filed Sep. 21, 1999, now abandoned, which claims the benefit of U.S. Provisional Application, U.S. Ser. No. 60/105,855, filed Oct. 27, 1998.

BACKGROUND OF THE INVENTION

The present invention relates generally to the preservation of pharmaceutical compositions. In particular, the present invention relates to the use of fatty acid/amino acid soaps to prevent or to reduce binding of the antimicrobial components of topically administrable pharmaceutical compositions to other components contained therein, thereby improving the antimicrobial efficacy of such compositions.

In recent years, a number of ophthalmic compositions have been introduced that contain a variety of components, such as carboxyvinyl polymers (e.g., Carbopol®), ion exchange resins (e.g., Amberlite®), or other large polyelectrolytes, which provide sustained release of the ophthalmic agent(s), as well as increased patient comfort. Such compositions are described, for example, in U.S. Pat. No. 4,911,920 (Jani et al.). Although these compositions are comfortable and have sustained release characteristics, cationic antimicrobials, such as benzalkonium chloride (BAC), which are often added as preservatives to such compositions, tend to bind to the anionic polyelectrolytes present in the formulations, resulting in loss of antimicrobial effectiveness.

Sarcosinate surfactants are composed of acylated sarcosines. Sarcosine ($CH_3$—NH—$CH_2$—COOH), an amino acid normally found in starfish and sea urchins, is chemically related to glycine ($NH_2$—$CH_2$—COOH), a basic amino acid in mammals. Common fatty acids and their derivatives utilized in the manufacture of sarcosinate surfactants are lauric, oleic, and myristic acids and their esters and halides. Because of their mildness, sarcosinate surfactants have been utilized in shampoos, mouthwashes, skin cleansers, sunscreens, aerosol shaving lathers and other personal care products. To date, the main applications of these types of surfactants have been in the cosmetic industry. For example, European Patent Application No. 0 194 097 (Schmidt et al.), assigned to Procter & Gamble, mentions sodium lauroyl sarcosinate as the mild anionic surfactant utilized in an aerosol skin-cleansing and moisturizer mousse.

U.S. Pat. No. 5,520,920 (Castillo, et al.) discloses the use of certain modified sarcosinates and lactylates to enhance antimicrobial effectiveness of ophthalmic compositions, particularly in the case where cationic preservatives otherwise bind to anionic polyelectrolytes. The modified sarcosinates have the formula:

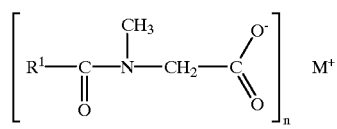

wherein: $R^1 = C_4-C_{27}$ saturated or unsaturated hydrocarbon; M=H or a pharmaceutically acceptable salt; and n=1, 2 or 3.

Representative modified sarcosinates include those sold under the Hamposyl® trade name, such as lauroyl sarcosine (Hamposyl® L), oleoyl sarcosine (Hamposyl® O), myristoyl sarcosine (Hamposyl® M), cocoyl sarcosine (Hamposyl® C.), stearoyl sarcosine (Hamposyl® S), and pelargodoyl sarcosine (Hamposyl® P). Representative lactylates include sodium capryl lactylate (Pationice® 122A).

Additional solutions to the problem of cationic preservative—anionic polyelectrolyte binding problem in topically administrable pharmaceutical compositions are desirable.

Fatty acid/amino acid soaps are known and include, for example, those surfactants sold under the Aminosoap® trade name (Ajinomoto Co., Inc., Tokyo, Japan). According to product brochures, Aminosoape surfactants are used in hair and body care (hair shampoo, body wash and bath foam), facial care (facial cleanser, facial washing foam, facial washing creme, and make-up remover), and household and health care.

SUMMARY OF THE INVENTION

The present invention provides a method of enhancing the preservative efficacy of topically administrable pharmaceutical compositions containing an anionic polyelectrolyte and a cationic preservative, but lacking a phospholipid. According to the method of the present invention, a fatty acid/amino acid soap is added to the topically administrable pharmaceutical composition.

Although the Applicants do not wish to be bound to a particular theory, it is believed that the addition of fatty acid/amino acid soaps to the compositions results in the release of the bound cationic preservative from the anionic polyelctrolyte by the formation of a loose and reversible surfactant-preservative complex. The surfactant-preservative complex has antimicrobial effectiveness. Alternatively, the soaps may themselves possess antimicrobial activity.

Regardless of the mechanism, the fatty acid/amino acid soaps of the present invention improve the preservative efficacy of topically administrable pharmaceutical compositions. Accordingly, the present invention also relates to topically administrable pharmaceutical compositions containing one or more pharmaceutically active agents, an anionic polyelectrolyte, a cationic preservative, and a fatty acid/amino acid soap.

DETAILED DESCRIPTION OF THE INVENTION

Unless indicated otherwise, all amounts of composition ingredients expressed in percentage terms are expressed as weight/weight.

Fatty acid/amino acid soaps useful in the preservative systems of the present invention are those wherein the fatty acid component is derived from a $C_8-C_{24}$ fatty acid and the amino acid component is selected from the group consisting of lysine and arginine. Preferably, the fatty acid component is selected from the group consisting of cocoyl, linoleoyl, lauroyl, myristoyl, stearoyl, oleoyl, and pelargodoyl fatty acid residues. Such fatty acid/amino acid soaps are commercially available or can be made by known methods. For example, the soap where the fatty acid component is cocoyl and the amino acid component is derived from arginine is commercially available as AMINOSOAP AR-12 from Ajinomoto Co., Inc. (Tokyo, Japan). The soap where the fatty acid component is cocoyl and the amino acid component is derived from lysine is available as AMINOSOAP LYC-12.

In general, the amount of fatty acid/amino acid soap present in the compositions of the present invention is from about 0.001 to about 1%, preferably from about 0.01 to about 0.2%, and most preferably from about 0.03 to about 0.12%. For topical ophthalmic preparations, the concentration of the fatty acid/amino acid soap should not be so high that it causes severe discomfort.

The compositions of the present invention contain cationic antimicrobials and anionic polyelectrolytes. Cationic antimicrobials are known in the art and include, but are not limited to, quaternary ammonium compounds, such as benzalkonium chloride and polyquaternium-1. Anionic polyelectrolytes include high molecular weight, anionic mucomimetic polymers (e.g., carboxyvinyl polymers such as Carbopol®), polystyrene sulfonic acid polymers, cationic exchange resins (e.g., Amberlite® or Dowex®), and the like.

High molecular weight, anionic mucomimetic polymers have a molecular weight between about 50,000 and 6 million. The polymers are characterized as having carboxylic acid functional groups and preferably contain between 2 and 7 carbon atoms per functional group. Suitable high molecular weight, anionic polymers are carboxyvinyl polymers, preferably those called Carbomers, e.g., Carbopol® (B.F. Goodrich Co., Cleveland, Ohio). Specifically preferred are Carbopol® 934P, Carbopole 974P and Carbopol® 940. Other suitable high molecular weight, anionic polymers include: alginates, carrageenans, natural gums (xanthan, karaya and tragacanth) and carboxy methyl cellulose. Such polymers will typically be employed in an amount between about 0.05 and about 6%, depending on the desired viscosity of the composition. Pourable liquid compositions generally comprise an amount of the polymer between about 0.05 and about 2%.

Cation exchange resins are characterized as either strongly acidic, such as those having sulfonic acid or sulfuric acid functionality, or weakly acidic, such as those having carboxylic acid functionality. Such resins are readily available, for example, from Rohm & Haas (Philadelphia, Pa.) under the name Amberlitee and from Dow Chemical Co. (Midland, Mich.) under the name Dowex®. The average particle size of the commercially available forms of the resins is about 40 to 150 microns. The particle size of the resin is critical for topically administrable ophthalmic compositions. Accordingly, for topically administrable ophthalmic compositions, commercially available resin particles are reduced by known techniques, including ball milling, to a particle size of about 20 μm or less such that the average particle size is <10 μm, and are preferably reduced to a particle size of about 10 μm or less. Ion exchange resins are typically used in an amount from about 0.05 to about 10%.

Anionic mucomimetic polymers and cation exchange resins are discussed in greater detail in U.S. Pat. No. 4,911,920 issued Mar. 27, 1990, the entire contents of which are hereby incorporated by reference herein.

The polystyrene sulfonic acid polymers (and their salts) useful in the compositions of the present invention comprise the following repeating unit:

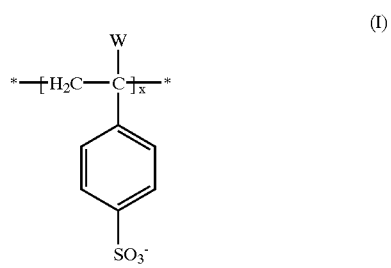

wherein: W=H or $CH_3$; and
x=an integer such that the molecular weight of the polystyrene sulfonic acid polymer is from about 10,000 to 1.6 million.

In the preferred polystyrene sulfonic acid polymers of formula I, W=H and the molecular weight is between about 500,000 to about 1,000,000, preferably about 600,000. If present in the compositions of the present invention, the polystyrene sulfonic acid polymers of formula I comprise less than about 8%, preferably less than about 5%.

The active ingredient or ingredients that can be included in the compositions of the present invention include all ophthalmic, dermatological, otic or nasal agents that can be topically applied. For example, such ophthalmic agents include (but are not limited to): anti-glaucoma agents, such as beta-blockers (e.g., betaxolol and timolol), muscarinics (e.g., pilocarpine), prostaglandins, carbonic anhydrase inhibitors (e.g., acetazolamide, methazolamide and ethoxzolamide), dopaminergic agonists and antagonists, and alpha adrenergic receptor agonists, such as para-amino clonidine (also known as apraclonidine) and brimonidine; anti-infectives, such as ciprofloxacin; non-steroidal and steroidal anti-inflammatories, such as suprofen, ketorolac, dexamethasone, rimexolone and tetrahydrocortisol; proteins; growth factors, such as EGF; and anti-allergic agents, such as cromolyn sodium, emedastine and olopatadine. Compositions of the present invention may also include combinations of active ingredients. Most preferred are topically administrable ophthalmic compositions.

The compositions of the present invention can also include other components, for example, pharmaceutically acceptable buffers; tonicity agents; comfort-enhancing agents; solubilizing aids; pH adjusting agents; antioxidants; and stabilizing agents. The compositions may also contain additional preservatives (in conjunction with the cationic preservatives addressed above). As will be appreciated by those skilled in the art, the compositions may be formulated in various dosage forms suitable for topical delivery, including solutions, suspensions, emulsions, and gels.

The compositions of the present invention do not contain a phospholipid.

The following examples are presented to illustrate further various aspects of the present invention, but are not intended to limit the scope of the invention in any respect.

EXAMPLE 1

| Ingredient | Concentration (%) |
| --- | --- |
| Betaxolol HCl | 0.28 |
| Amberlite IRP-69 | 0.25 |
| Carbopol 974P | 0.45 |
| Cocoyl N-Lysine* | 0.03 |

| -continued | |
|---|---|
| Ingredient | Concentration (%) |
| Boric Acid | 0.4 |
| Mannitol | 4.5 |
| Edetate Disodium | 0.01 |
| Benzalkonium Chloride | 0.01 |
| NaOH and/or HCl | q.s. to pH 6.5 |
| Purified Water | q.s. to 100 |

*Aminosoap LYC-12

Preparation:

0.42 g betaxolol hydrochloride, 0.375 g amberlite IRP 69 resin, 0.60 g boric acid, 6.75 g mannitol, 0.015 g disodium EDTA were combined in 40 mL water and stirred for 30 minutes. To this was added 1.06 g 1% BAC stock solution, 33.8 g of 2% carbopol 974P stock slurry, and 0.15 g of a 30% solution of cocoyl lysine (Aminosoap LYC-12 from Ajinomoto.) The pH of the formulation was adjusted to 6.5 by the addition of 2.2 mL of 5N NaOH and the final batch amount was brought to 150 mL with water. The formulation was sterilized for 60 minutes in an autoclave oven at 121° C.

EXAMPLE 2

| Ingredient | Concentration (%) |
|---|---|
| Betaxolol HCl | 0.28 |
| Amberlite IRP-69 | 0.25 |
| Carbopol 974P | 0.45 |
| Cocoyl N-Lysine* | 0.03 |
| Boric Acid | 0.4 |
| Mannitol | 4.5 |
| Edetate Disodium | 0.01 |
| Benzalkonium Chloride | 0.01 + 10% xs |
| Tromethamine | q.s. to pH 6.5 |
| Purified Water | q.s. to 100 |

*Aminosoap LYC-12

Preparation:

0.84 g betaxolol hydrochloride and 0.75 g amberlite IRP 69 resin were combined in ~30 mL water and stirred for 30 minutes. To this was added (in order indicated) 67.5 g of 2% carbopol 974P stock slurry, 13.5 g mannitol, 0.03 g disodium EDTA, 1.20 g boric acid, and 2.97 g of 1.11% benzalkonium chloride stock solution. To this was added 25 mL of 10% tromethamine solution, and the mixture was allowed to stir for 2 hours. The formulation was brought to 260 g by the addition of water, and the pH was adjusted to 6.0 by the dropwise addition of 10% tromethamine solution. To the formulation was added 0.3 g of 30% cocoyl lysine solution (Aminosoap LYC-12 from Ajinomoto). The formulation was adjusted to pH 6.5 by the dropwise addition of 10% tromethamine solution, and the final batch amount was then adjusted tog 300 g by the addition of water. The formulation was steam sterilized for 60 minutes at 121° C. in an autoclave oven.

The formulation of Example 2 was found to have the following characteristics.

| % label benzalkonium chloride | 110% (prepared to contain 10% excess) |
|---|---|
| % unbound benzalkonium chloride | 0.76% |
| % label betaxolol | 100% |
| % unbound betaxolol | 28% |

| -continued | |
|---|---|
| osmolality | 312 mOsm/Kg |
| viscosity | 138 cps |

EXAMPLE 3

| Representative Formulation | |
|---|---|
| Ingredient | Concentration (%) |
| Betaxolol HCl | 0.28 |
| Amberlite IRP-69 | 0.25 |
| Carbopol 974P | 0.45 |
| Cocoyl N-Lysine* | 0.06 |
| Boric Acid | 0.4 |
| Mannitol | 4.5 |
| Edetate Disodium | 0.01 |
| Benzalkonium Chloride | 0.01 |
| NaOH and/or HCl | q.s. to pH 7.2 |
| Purified Water | q.s. to 100 |

*Aminosoap LYC-12

EXAMPLE 4

| Ingredient | Concentration (%) |
|---|---|
| Betaxolol HCl | 0.28 |
| Amberlite IRP-69 | 0.25 |
| Carbopol 974P | 0.45 |
| Cocoyl N-Arginine* | 0.03 |
| Boric Acid | 0.4 |
| Mannitol | 4.15 |
| Edetate Disodium | 0.01 |
| Benzalkonium Chloride | 0.01 + 10% xs |
| Tromethamine | q.s. to pH 6.5 |
| Purified Water | q.s. to 100 |

*Aminosoap AR-12

EXAMPLE 5

| Representative Formulation | |
|---|---|
| Ingredient | Concentration (%) |
| Betaxolol HCl | 0.28 |
| Brinzolamide | 1 |
| Amberlite IRP-69 | 0.25 |
| Carbopol 974 P | 0.45 |
| Boric Acid | 0.4 |
| Mannitol | 4.5 |
| Cocoyl N-Lysine* | 0.06 |
| Edetate Disodium | 0.01 |
| Benzalkonium Chloride | 0.01 |
| NaOH and/or HCl | q.s. to pH 6.5 |
| Purified Water | q.s. to 100 |

*Aminosoap LYC-12

COMPARATIVE EXAMPLE 1

| Ingredient | Concentration (%) |
| --- | --- |
| Betaxolol HCl | 0.28 |
| Amberlite IRP-69 | 0.25 |
| Carbopol 974P | 0.45 |
| Boric Acid | 0.4 |
| Mannitol | 4.5 |
| Edetate Disodium | 0.01 |
| Benzalkonium Chloride | 0.01 |
| NaOH and/or HCl | q.s. to pH 6.5 |
| Purified Water | q.s. to 100 |

COMPARATIVE EXAMPLE 2

| Ingredient | Concentration (%) |
| --- | --- |
| Betaxolol HCl | 0.28 |
| Benzalkonium Chloride | 0.01 |
| Carbopol 974P | 0.45 |
| Amberlite IRP-69 | 0.25 |
| Triethanolamine Cocoyl Glutamate* | 0.03 |
| Boric Acid | 0.4 |
| Mannitol | 4.5 |
| Edetate Disodium | 0.01 |
| NaOH and/or HCl | q.s. to pH 6.5 |
| Purified Water | q.s. to 100 |

*Amisoft CT-12

COMPARATIVE EXAMPLE 3

| Ingredient | Concentration (%) |
| --- | --- |
| Betaxolol HCl | 0.28 |
| Benzalkonium Chloride | 0.01 + 10% xs |
| Sodium Lauroyl Glutamate* | 0.03 |
| Carbopol 974P | 0.45 |
| Amberlite IRP-69 | 0.25 |
| Boric Acid | 0.4 |
| Mannitol | 4.15 |
| Edetate Disodium | 0.01 |
| Tromethamine | q.s. to pH 6.5 |
| Purified Water | q.s. to 100 |

*Amisoft LS-11

COMPARATIVE EXAMPLE 4

| Ingredient | Concentration (%) |
| --- | --- |
| Betaxolol HCl | 0.28 |
| Benzalkonium Chloride | 0.01 + 10% xs |
| Sodium Myristoyl Glutamate* | 0.03 |
| Carbopol 974P | 0.45 |
| Amberlite IRP-69 | 0.25 |
| Boric Acid | 0.4 |
| Mannitol | 4.15 |
| Edetate Disodium | 0.01 |
| Tromethamine | q.s. to 6.5 |
| Purified Water | q.s. to 100 |

*Amisoft MS-11

COMPARATIVE EXAMPLE 5

| Ingredient | Concentration (%) |
| --- | --- |
| Betaxolol HCl | 0.28 |
| Benzalkonium Chloride | 0.01 + 10% xs |
| Sodium Stearoyl Glutamate* | 0.03 |
| Carbopol 974P | 0.45 |
| Amberlite IRP-69 | 0.25 |
| Boric Acid | 0.4 |
| Mannitol | 4.15 |
| Edetate Disodium | 0.01 |
| Tromethamine | q.s. to pH 6.5 |
| Purified Water | q.s. to 100 |

*Amisoft HS-11

COMPARATIVE EXAMPLE 6

| Ingredient | Concentration (%) |
| --- | --- |
| Betaxolol HCl | 0.28 |
| Benzalkonium Chloride | 0.01 + 10% xs |
| Carbopol 974P | 0.45 |
| Triethanolamine Cocoyl Glutamate* | 0.03 |
| Amberlite IRP-69 | 0.25 |
| Boric Acid | 0.4 |
| Mannitol | 4.5 |
| Edetate Disodium | 0.01 |
| Tromethamine | q.s. to pH 6.5 |
| Purified Water | q.s. to 100 |

*Amisoft CT-12

COMPARATIVE EXAMPLE 7

| Ingredient | Concentration (%) |
| --- | --- |
| Benzalkonium Chloride | 0.01 |
| Mannitol | 5 |
| Purified Water | q.s. to 100 |

COMPARATIVE EXAMPLE 8

| Ingredient | Concentration (%) |
| --- | --- |
| Benzalkonium Chloride | 0.01 |
| Boric Acid | 0.4 |
| Mannitol | 4.9 |
| Tromethamine | 0.726 |
| Edetate Disodium | 0.01 |
| Purified Water | q.s. to 100 |

EXAMPLE 6

Antimicrobial preservative effectiveness was determined using an organism challenge test according to the methods described in the United States Pharmacopeia (USP) and European Pharmacopoeia (Ph.Eur.). Samples were inoculated with known levels of one or more of the following: gram-positive (*Staphylococcus aureus* ATCC 6538) and gram-negative (*Pseudomonas aeruginosa* ATCC 9027 and *Escherichia coli* ATCC 8739) vegetative bacteria, yeast (*Candida albicans* ATCC 10231) and mold (*Aspergillus niger* ATCC 16404). The samples were then pulled at specified intervals to determine if the antimicrobial preservative system was capable of killing or inhibiting the propagation of organisms purposely introduced into the formulation. The rate or level of antimicrobial activity determined compliance with the USP and/or Ph.Eur. preservative efficacy standards for ophthalmic preparations.

The compendial preservative standards for ophthalmic preparations are presented below:

| | Log Reduction of Organism Population | | |
|---|---|---|---|
| Time Pull | USP | Ph.Eur. A (Target) | Ph.Eur. B (Min) |
| For Bacteria: | | | |
| 6 hours | — | 2 | — |
| 24 hours | — | 3 | 1 |
| 7 days | — | — | 3 |
| 14 days | 3 | — | — |
| 28 days | NI | NR | NI |
| For Fungi: | | | |
| 7 days | — | 2 | — |
| 14 days | NI | — | 1 |
| 28 days | NI | NI | NI |

NR = No organisms recovered
NI = No increase at this or any following time pulls
— = No requirement at this time pull The results of the microorganism challenge tests are shown in Tables 1 and 2 below.

TABLE 1

| | Preservative Efficacy Standard | | |
|---|---|---|---|
| Formulation | USP | Ph.Eur. B (Minimum) | Ph.Eur. A (Target) |
| Example 1* | Pass | Pass | Fail |
| Example 2 | Pass | Pass | Fail |
| Example 4* | Pass | Pass | Fail |
| Comp. Ex. 1 | Pass | Fail | Fail |

*Projected results based on S. aureus, P. aeruginosa and A. niger data

TABLE 2

| | Organism (7 day results - log reduction) | | | | |
|---|---|---|---|---|---|
| Formulation | S. aureus | P. aeruginosa | E. coli | C. albicans | A. niger |
| Comp. Ex. 2 | 2.9 | 5.0 | — | — | 1.3 |
| Comp. Ex. 3 | 0.0 | 5.0 | — | — | 2.9 |
| Comp. Ex. 4 | 1.5 | 5.0 | — | — | 3.5 |
| Comp. Ex. 5 | 2.1 | 5.0 | — | — | 3.6 |
| Comp. Ex. 6 | 0.5 | 5.0 | 5.0 | 1.6 | 2.0 |
| Comp. Ex. 7 | 4.8 | 4.7 | 4.9 | 4.7 | 2.5 |
| Comp. Ex. 8 | 4.8 | 4.7 | 4.9 | 4.7 | 3.7 |

The invention in its broader aspects is not limited to the specific details shown and described above. Departures may be made from such details within the scope of the accompanying claims without departing from the principles of the invention and without sacrificing its advantages.

We claim:

1. A method of improving or enhancing the antimicrobial efficacy of a topically administrable pharmaceutical composition comprising a cationic antimicrobial, an anionic polyelectrolyte and an active ingredient, wherein the method comprises adding to the composition an antimicrobial-enhancing amount of a fatty acid/amino acid soap having a fatty acid component selected from the group consisting of $C_8$–$C_{24}$ fatty acids and an amino acid component selected from the group consisting of lysine and arginine, wherein the fatty acid component and the amino acid component are ionically associated in the soap, and wherein the antimicrobial-enhancing amount is from about 0.001 to about 1%, provided that the composition does not contain a phospholipid.

2. The method of claim 1 wherein the fatty acid component is selected from the group consisting of cocoyl; linoleoyl; lauroyl; myristoyl; stearoyl; oleoyl; and pelargodoyl fatty acid residues.

3. The method of claim 2 wherein the fatty acid component is cocoyl.

4. The method of claim 1 wherein the antimicrobial-enhancing amount of fatty acid/amino acid soap is from about 0.01 to about 0.2%.

5. The method of claim 4 wherein the antimicrobial-enhancing amount of fatty acid/amino acid soap is from about 0.03 to about 0.12%.

6. The method of claim 1 wherein the anionic polyelectrolyte is selected from the group consisting of: carboxyvinyl polymers; xanthan gum; polystyrene sulfonic acid polymers; and cationic exchange resins.

7. The method of claim 1 wherein the topically administrable pharmaceutical composition further comprises one or more active ingredients selected from the group consisting of ophthalmic; dermatological; otic; and nasal agents.

8. The method of claim 7 wherein the topically administrable pharmaceutical composition comprises an ophthalmic agent selected from the group consisting of anti-glaucoma agents; anti-infectives; non-steroidal and steroidal anti-inflammatories; proteins; growth factors; and anti-allergic agents.

9. The method of claim 8 wherein the topically administrable pharmaceutical composition further comprises one or more ingredients selected from the group consisting of pharmaceutically acceptable buffers; tonicity agents; comfort-enhancing agents; solubilizing aids; pH adjusting agents; antioxidants; and stabilizing agents.

10. A topically administrable pharmaceutical composition comprising a cationic antimicrobial, an anionic polyelectrolyte, an active ingredient, and an antimicrobial-enhancing amount of a fatty acid/amino acid soap having a fatty acid component selected from the group consisting of $C_8$–$C_{24}$ fatty acids and an amino acid component selected from the group consisting of lysine and arginine, wherein the fatty acid component and the amino acid component are ionically associated in the soap, and wherein the antimicrobial-enhancing amount is from about 0.001 to about 1%, provided that the composition does not contain a phospholipid.

11. The composition of claim 10 wherein the fatty acid component is selected from the group consisting of cocoyl; linoleoyl; lauroyl; myristoyl; stearoyl; oleoyl; and pelargodoyl fatty acid residues.

12. The composition of claim 11 wherein the fatty acid component is cocoyl.

13. The composition of claim 10 wherein the antimicrobial—enhancing amount of fatty acid/amino acid soap is from about 0.01 to about 0.2%.

14. The composition of claim 13 wherein the antimicrobial—enhancing amount of fatty acid/amino acid soap is from about 0.03 to about 0.12%.

15. The composition of claim 10 wherein the anionic polyelectrolyte is selected from the group consisting of:

carboxyvinyl polymers; xanthan gum; polystyrene sulfonic acid polymers; and cationic exchange resins.

16. The composition of claim 10 wherein the active ingredient is selected from the group consisting of anti-glaucoma agents; anti-infectives; non-steroidal and steroidal anti-inflammatories; proteins; growth factors; and anti-allergic agents.

17. The composition of claim 10 wherein the composition further comprises one or more ingredients selected from the group consisting of pharmaceutically acceptable buffers; tonicity agents; comfort-enhancing agents; solubilizing aids; pH adjusting agents; antioxidants; and stabilizing agents.

* * * * *